US009023006B2

(12) United States Patent
Takino et al.

(10) Patent No.: US 9,023,006 B2
(45) Date of Patent: May 5, 2015

(54) WEARING ARTICLE WITH BONDED GASKET ELASTIC

(75) Inventors: Shunsuke Takino, Kagawa (JP); Shunsuke Masaki, Kagawa (JP)

(73) Assignee: Unicharm Corporation, Ehime (JP)

( * ) Notice: Subject to any disclaimer, the term of this patent is extended or adjusted under 35 U.S.C. 154(b) by 141 days.

(21) Appl. No.: 13/499,268

(22) PCT Filed: Sep. 27, 2010

(86) PCT No.: PCT/JP2010/005797
§ 371 (c)(1),
(2), (4) Date: Mar. 29, 2012

(87) PCT Pub. No.: WO2011/039988
PCT Pub. Date: Apr. 7, 2011

(65) Prior Publication Data
US 2012/0191057 A1    Jul. 26, 2012

(30) Foreign Application Priority Data

Sep. 30, 2009    (JP) ................................ 2009-228873

(51) Int. Cl.
*A61F 13/49*    (2006.01)
*A61F 13/494*    (2006.01)

(52) U.S. Cl.
CPC ..... *A61F 13/49413* (2013.01); *A61F 13/49061* (2013.01); *A61F 2013/49026* (2013.01); *A61F 13/49011* (2013.01)

(58) Field of Classification Search
CPC ................... A61F 13/49011; A61F 13/49061; A61F 13/49413; A61F 2013/49026
USPC .................. 604/385.24–385.3, 393, 394, 396
See application file for complete search history.

(56) References Cited

U.S. PATENT DOCUMENTS

| 7,201,744 | B2 * | 4/2007 | Van Gompel et al. | ........ 604/391 |
| 2002/0147439 | A1 * | 10/2002 | Tanaka et al. | ................. 604/398 |

(Continued)

FOREIGN PATENT DOCUMENTS

| EP | 2 275 065 A1 | 1/2011 |
| JP | 2002-172134 | 6/2002 |

(Continued)

OTHER PUBLICATIONS

International Search Report from corresponding PCT application No. PCTJP2010/005797 dated Nov. 22, 2010 (3 pgs).

(Continued)

*Primary Examiner* — Tan-Uyen (Jackie) T Ho
*Assistant Examiner* — Kathryn E Ditmer
(74) *Attorney, Agent, or Firm* — Brinks Gilson & Lione

(57) ABSTRACT

The present invention aims to provide a wearing article adapted to prevent unintentional displacement of a crotch region relative to front and rear waist regions by elastics attached to the crotch region. A diaper includes front and rear waist members, a crotch member by the intermediary of which the front and rear waist members are connected with each other. The rear waist member is formed with a waist fit section and an appendix section. Of the crotch member, front and rear ends including front and rear end flaps are bonded to the front and rear waist members, respectively, to form front and rear bonded regions. Both side flaps are provided on respective inner surfaces thereof with gasket elastics attached thereto. Each of the gasket elastic overlaps at one end with a part of the front waist elastic and overlaps at the other end with a part of the appendix section elastic. Furthermore, the one end overlaps with the front bonded region and the other end overlaps with the rear bonded regions.

8 Claims, 7 Drawing Sheets

(56) References Cited

U.S. PATENT DOCUMENTS

| | | |
|---|---|---|
| 2004/0015146 A1 | 1/2004 | Torigoshi et al. |
| 2006/0030831 A1 | 2/2006 | Matsuda et al. |
| 2007/0073262 A1* | 3/2007 | Babusik et al. ............... 604/396 |
| 2010/0106123 A1* | 4/2010 | Fukae ........................... 604/373 |
| 2010/0286646 A1* | 11/2010 | Takino et al. .............. 604/385.3 |
| 2011/0066127 A1* | 3/2011 | Kuwano et al. ............ 604/385.3 |

FOREIGN PATENT DOCUMENTS

| | | | |
|---|---|---|---|
| JP | 2004329238 A | * | 11/2004 |
| JP | 2004-350809 | | 12/2004 |
| JP | 2008-508082 A | | 3/2008 |
| JP | 2008-194161 | | 8/2008 |
| JP | 2008-253285 | | 10/2008 |
| JP | 2008-253583 | | 10/2008 |
| JP | 2009-106666 | | 5/2009 |
| WO | WO 2008108270 A1 | * | 9/2008 |
| WO | WO 2009/031393 A1 | | 3/2009 |
| WO | WO 2009031393 A1 | * | 3/2009 |
| WO | WO 2009/084643 A1 | | 7/2009 |

OTHER PUBLICATIONS

European Supplementary Search Report from corresponding European application No. 10820110.4 dated Jul. 18, 2014 (8 pgs).

* cited by examiner

WEARING ARTICLE WITH BONDED GASKET ELASTIC

RELATED APPLICATION

This application is a 35 U.S.C. §371 national phase filling of International Patent Application No. PCT/JP2010/005797filed Sep. 27, 2010, through which and to which priority is claimed under 35 U.S.C. §119 to Japanese Patent Application No. 2009-228873, filed Sep. 30, 2009.

TECHNICAL FIELD

The present invention relates to wearing articles and particularly to wearing articles such as disposable diapers, toilet-training pants, incontinent briefs or the like.

RELATED ART

Disposable diapers each comprising a front waist panel, a rear waist panel and an intermediate panel connecting these front and rear waist panels is known. For example, PATENT DOCUMENT 1 (JP 2008-508082 A) discloses such a disposable diaper including an intermediate panel having leg elastics attached thereto along transversely opposite side edges thereof to extend in a longitudinal direction. The respective side edges of the intermediate panel define respective leg-openings so that the peripheral edges of the leg-openings may fit around the wearer's thighs under contraction of the leg elastics and thereby prevent bodily fluids such as urine from leaking out from the diaper.

Concerning the leg elastics, PATENT DOCUMENT 1 (JP 2008-508082 A) discloses that these elastics may be attached to the intermediate panel at appropriate positions in the crotch region of the diaper or fully along the transversely opposite side edges of the intermediate panel. However, no description of the specific range in which the leg elastics may be attached to the intermediate panel can be found in the disclosure of PATENT DOCUMENT 1 (JP 2008-508082 A).

CITATION LIST

Patent Literature

[PATENT DOCUMENT 1] JP 2008-508082 A

SUMMARY

A wearing article in accordance with one or more embodiment of the present invention comprises a chassis, a liquid-absorbent structure and a pair of gasket cuffs, the chassis having a longitudinal direction, a transverse direction, a skin-facing side, a non-skin-facing side, a front waist region, a rear waist region and a crotch region extending between the front and rear waist regions, the liquid-absorbent structure extending across the crotch region into the front and rear waist regions, and the gasket cuffs being outboard of the liquid-absorbent structure in the transverse direction, wherein the front and rear waist regions include front and rear waist elastics attached thereto in a contractible manner in the transverse direction and the gasket cuffs include gasket elastics attached thereto in a contractible manner in the longitudinal direction.

In the wearing article described above, the rear waist region comprises a waist fit section extending in a vicinity of a waist opening and an appendix section arranged to be contiguous to the waist fit section and lying in the crotch region, wherein the rear waist elastic is attached to the waist fit section and the appendix section is provided with an appendix section elastic attached thereto in contractible manner in the transverse direction; and the gasket elastic has one end overlapping with and bonded to the front waist elastic and the other end overlapping with and bonded to the appendix section elastic.

DETAILED DESCRIPTION

<First Embodiment>

Details of the present invention will be more fully understood from the description of a disposable diaper as one of typical examples of the wearing article according to the present invention. A first embodiment of the present invention will be described with reference to FIGS. 1 through 8.

Figure 1:
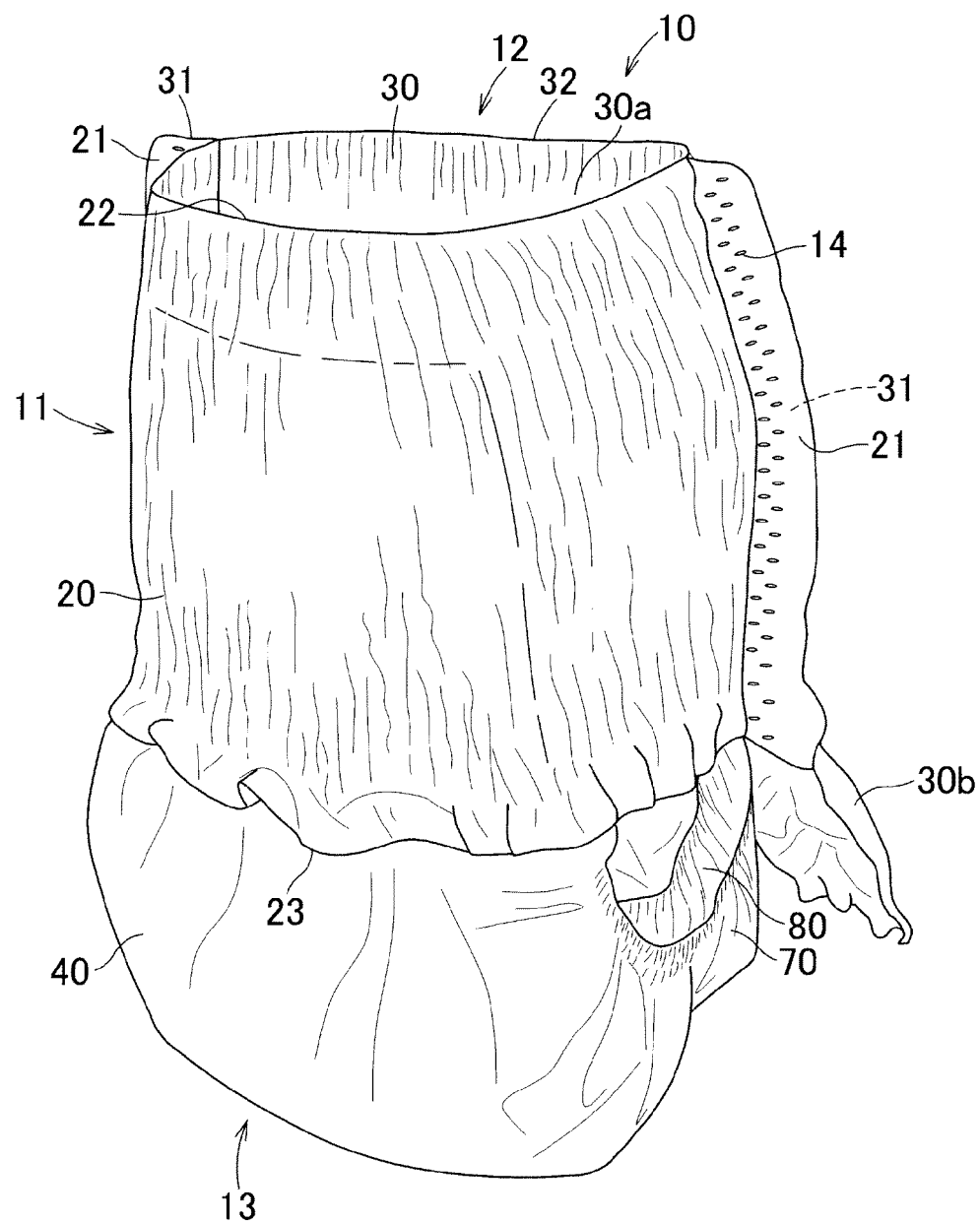
FIG. 1 is a perspective view of a diaper according to a first embodiment of the present invention.
Figure 2:
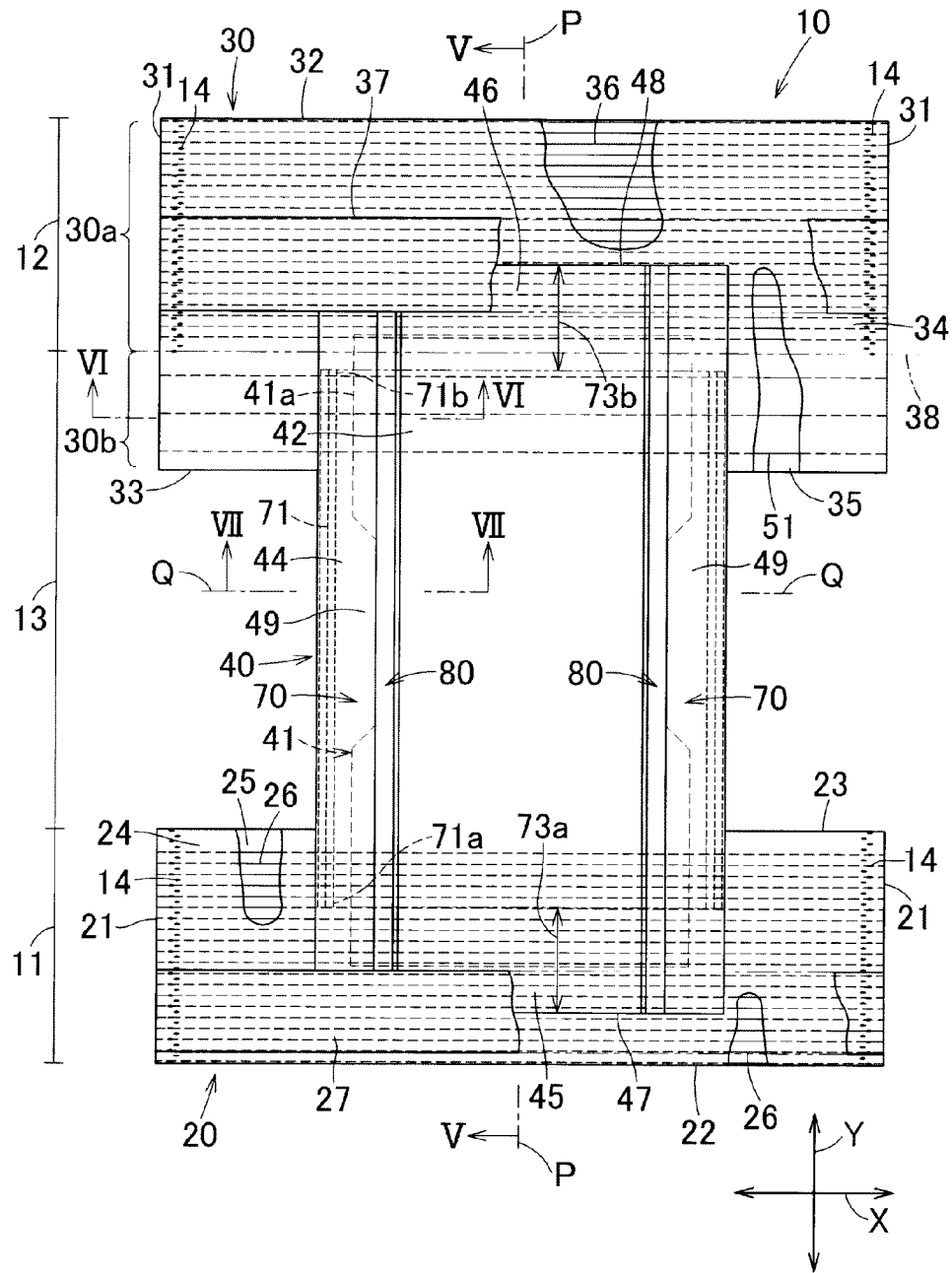
FIG. 2 is a plan view of the diaper as flatly developed and viewed from the skin-facing side of the diaper.
Figure 3:
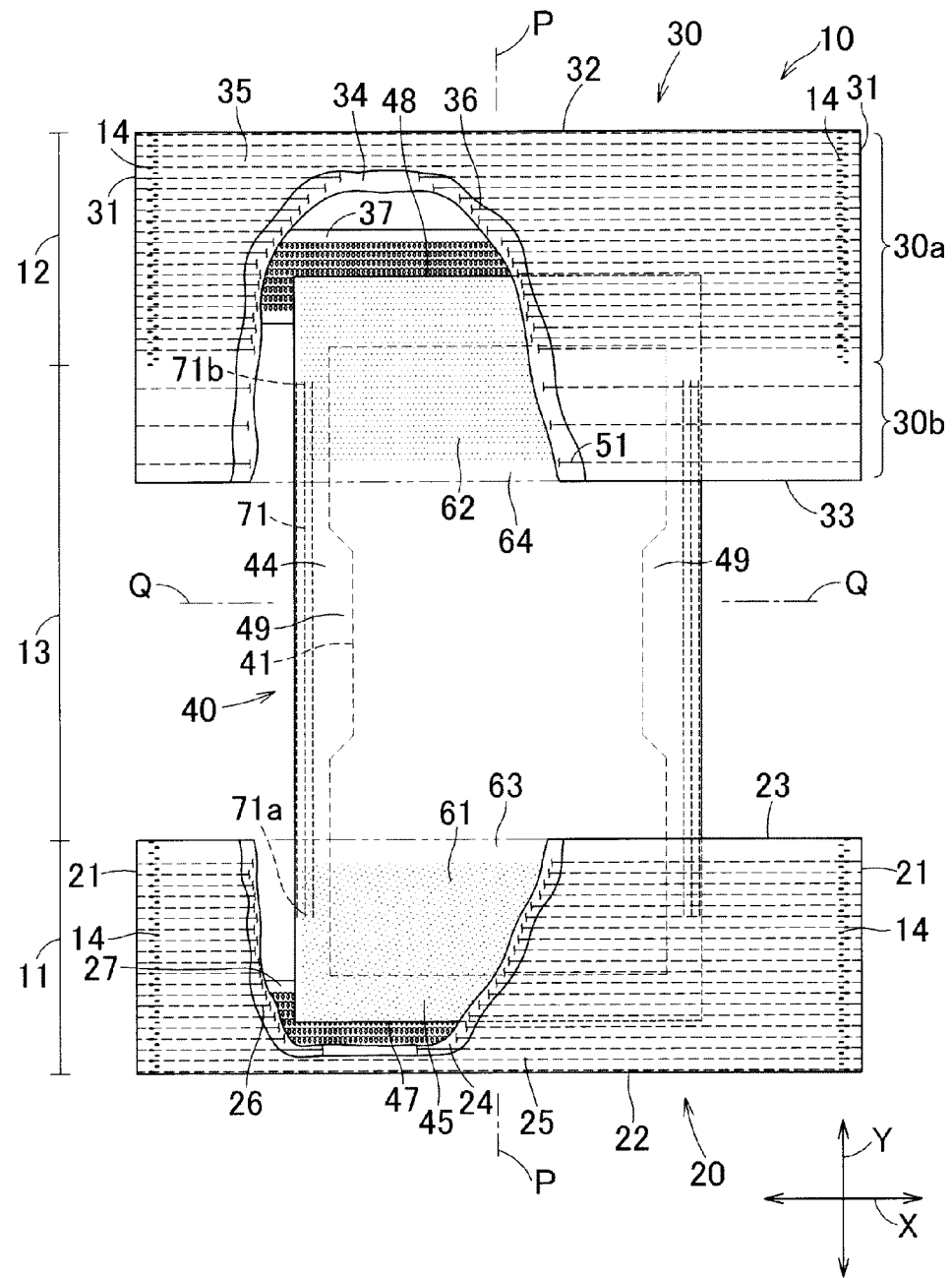
FIG. 3 is a plan view of the diaper as flatly developed and viewed from the non-skin-facing side of the diaper.
Figure 4:
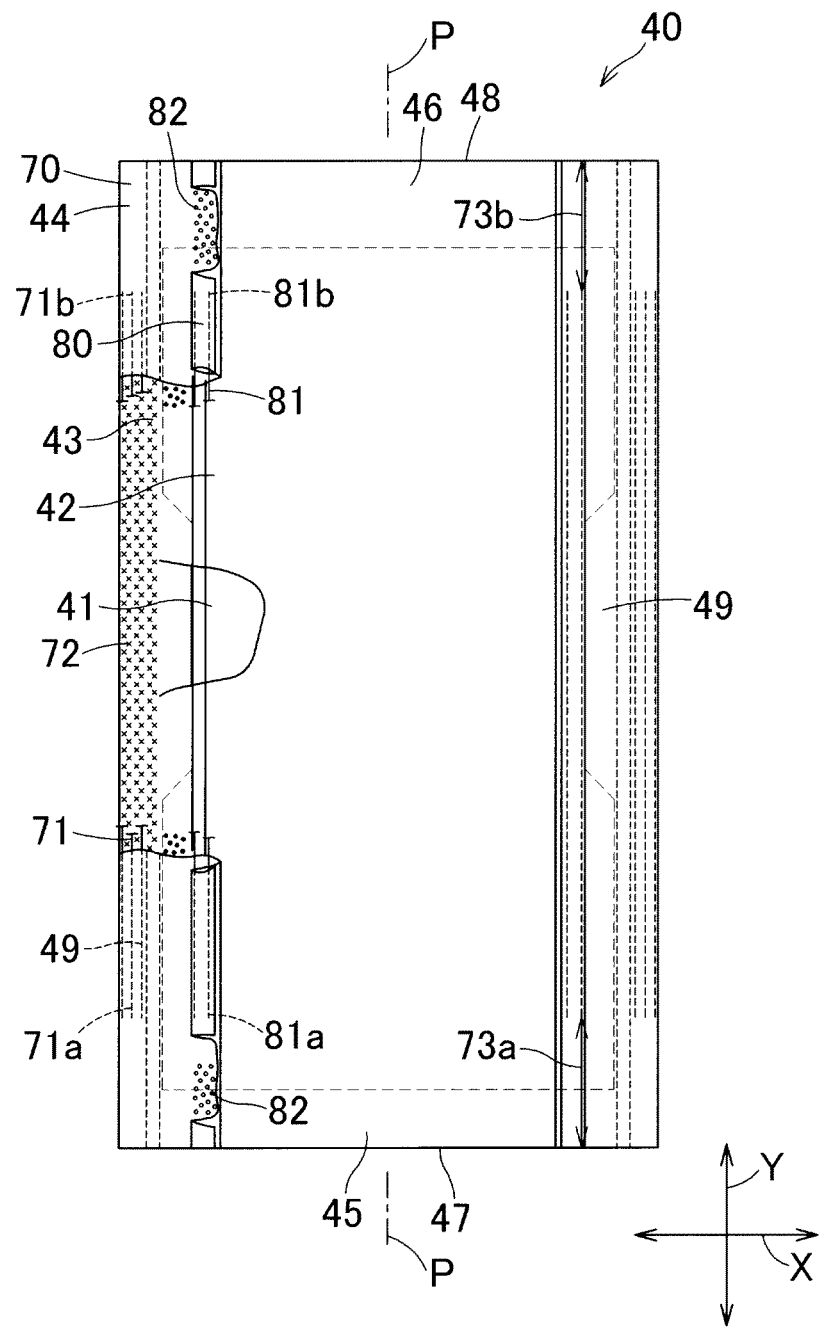
FIG. 4 is a diagram illustrating details of a crotch member.
Figure 5:
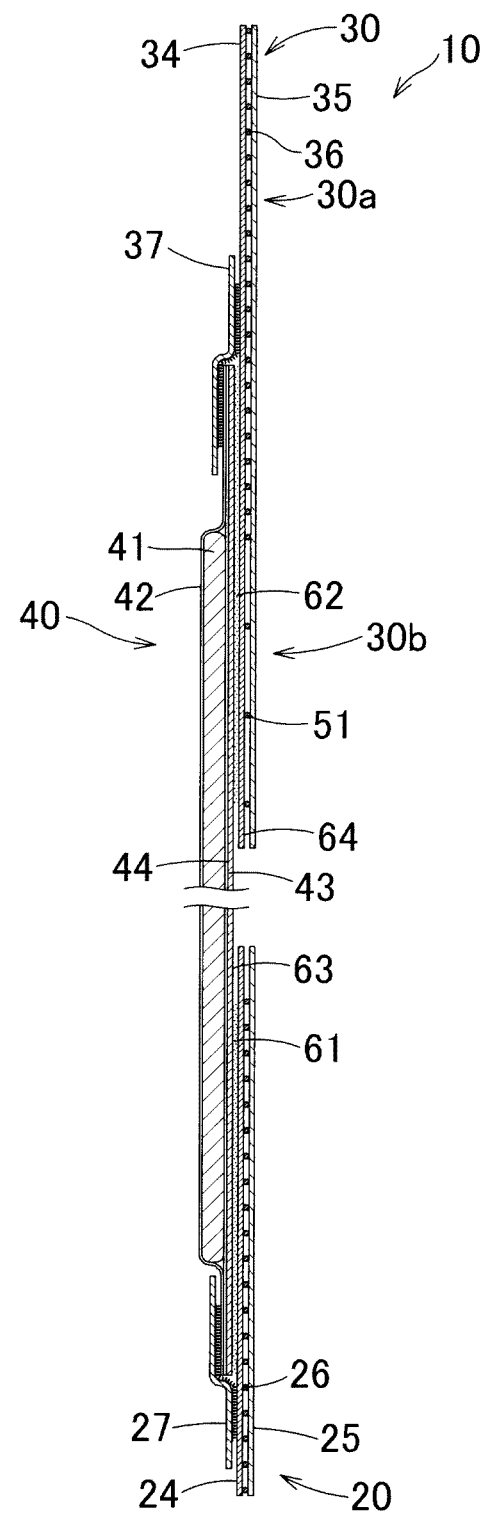
FIG. 5 is a sectional view taken along the line V-V in FIG. 2.
Figure 6:
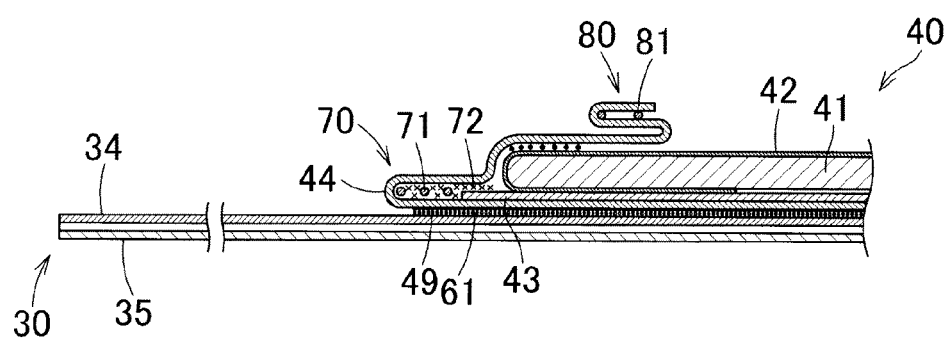
FIG. 6 is a sectional view taken along the line VI-VI in FIG. 2.
Figure 7:
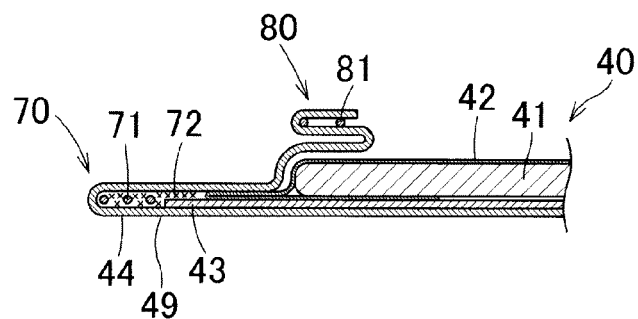
FIG. 7 is a sectional view taken along the line VII-VII in FIG. 2.
Figure 8:
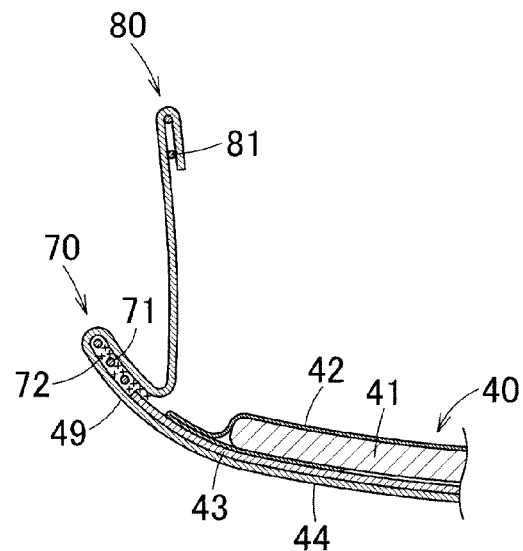
FIG. 8 is a view similar to FIG. 7 but under contractile force.

Referring to FIGS. 1-3, the diaper 10 has a longitudinal direction Y, a transverse direction X, a skin-facing side, a garment-facing side (non-skin-facing side), a front waist region 11, a rear waist region 12 and a crotch region 13 extending between the front and rear waist regions 11, 12. A length dimension of the diaper 10 in the transverse direction X is bisected by the imaginary longitudinal center line P-P and a length dimension of the diaper 10 in the longitudinal direction Y is bisected by the imaginary transverse center line Q-Q and the diaper 10 is shaped almost symmetric about the imaginary longitudinal center line P-P.

The diaper 10 comprises front and rear waist members 20, 30 spaced from each other in the longitudinal direction Y and a crotch member 40 by the intermediary of which the front and rear waist members 20, 30 are connected with each other. Side edges 21 of the front waist member 20 spaced from and opposite to each other in the transverse direction X may be joined to associated side edges 31 of the rear waist member 30 to form seams 14, in other words, to form a waist-opening and a pair of leg-openings.

The rear waist member 30 is dimensioned to be longer than the front waist region 20 in the longitudinal direction Y. Specifically, the rear waist member 30 comprises a waist fit section 30a and an appendix section 30b extending into the crotch region 13. With the diaper 10 having the front and rear waist members 20, 30 joined together along the respective side edges, the waist fit section 30a put flat together with the front waist member 20 and positioned to cover the wearer' rear waist and the appendix section 30b extends from the waist fit section 30a into the crotch region 13. A boundary of these waist fit section 30a and the appendix section 30b is indicated by an imaginary line 38 in FIG. 2. A length dimension in the longitudinal direction Y of the front waist member 20 and the waist fit section 30a is in a range of about 70 to 240 mm and, in this embodiment, about 105 mm. A length dimension of the appendix section 30b in the longitudinal direction Y is in a range of about 30 to 90 mm and, in this embodiment, about 60 mm. A width dimension of the appendix section 30b in the transverse direction X is almost the same as that of the waist fit section 30a so that the waist fit section 30a and the appendix section 30b may form together a rectangle.

A region defined between an outer end 22 and an inner end 23 of the front waist member 20 is designated as the front waist region 11, the waist fit section 30a defined between an outer end 32 and the imaginary line 38 is designated here as the rear waist region 12 and a region defined between the imaginary line 38 and the inner end 23 of the front waist member 20 is designated as the crotch region 13. The front and rear waist members 20, 30 and a part of the crotch member 40 cooperate together to form a chassis according to the present invention.

With the dimensional relation as has been described, the appendix section 30b extends downward to the lower ends of the respective leg-openings to cover the leg-openings and extends downward beyond gasket cuffs 70 and leak-barrier cuffs 80 to be described below in details.

The front waist member 20 and the waist fit section 30a respectively have a front waist elastic 26 and a rear waist elastic 36 each comprising a plurality of elastic strings extending in the transverse direction X and attached thereto under tension in a contractible manner. The elastic strings consisting of the front and rear waist elastics 26, 36 arranged to be spaced one from another in the longitudinal direction Y at a pitch in a range of about 3 to about 15 mm. In the present embodiment, this pitch is set to be about 5 mm. Both the front and rear waist elastics 26, 36 are set to have tensile stress in the regions adjacent to the front and rear ends 22, 32, respectively, higher than those in the other regions so that a peripheral edge of the waist-opening may be reliably put in close contact with the wearer's body and leakage of bodily fluids such as urine may be reliably prevented. As the front and rear waist elastics 26, 36, respectively, about three to twelve elastic strings each having fineness in a range of about 470 to 1240dtex may be used. In the present embodiment, five elastic strings each having fineness of about 470dtex are used as each of the front and rear elastics 26, 36. Respective four elastic strings counted from the front and rear ends 22, 32 are attached at a stretch ratio of about 2.6 and the elastic strings inboard of these four elastic strings in the longitudinal direction Y are attached at a stretch ratio of about 2.1. The stretch ratio of these elastic strings may be appropriately regulated in a range of about 1.8 to 3.5.

The appendix section 30b has an appendix section elastic 51 comprising a plurality of elastic strings extending in the transverse direction X and attached thereto under tension in a contractible manner. The elastic strings consisting of the appendix section elastic 51 are arranged to be spaced one from another in the longitudinal direction Y at a pitch in a range of about 10 to about 30 mm. In the present embodiment, the elastic strings of the appendix section elastic 51 are spaced one from another at a pitch larger than that of the front and rear waist elastics 26, 36, specifically of about 20 mm. This is for the reason that it is not essential to put the appendix section 30b in close contact with the wearer's body under high tensile stress. In addition, the number of the elastic strings of the appendix section elastic 51 may be reduced to prevent the appendix section 30b from increasing stiffness thereof. As the appendix section elastic 51, the elastic strings each having fineness in a range of about 470 to 1240dtex may be attached at a stretch ratio in a range of about 1.5 to 3.2. In the present embodiment, three elastic strings each having fineness of about 470dtex are used as the appendix section elastic 51, of which one elastic string is attached at a stretch ratio of about 2.1 to extending from the imaginary line 38 corresponding to the boundary between the waist fit section 30a and the appendix section 30b toward the inner end 33 of the rear waist panel and the other two elastic strings are attached at a stretch ratio of about 2.4. In this manner, the zone of the appendix section 30b in the vicinity of the imaginary line 38 has the stretch ratio smaller than that of the zone of the appendix section 30b in the vicinity of the inner end 33 of the rear waist member 30.

The appendix section elastic 51 may be coated on itself with adhesive to be bonded to the inner and outer sheets 34, 35 of the rear waist member 30. By adhesive applied on the elastic 51 in this manner, these inner and outer sheets 34, 35 are also bonded to each other. In consequence, it is assured that the appendix section elastic 51 can be prevented from falling off and, in addition, stiffness of the sheets can be prevented from excessively increasing due to application of excessive quantity of adhesive. The front and rear waist elastics 26, 36 may be bonded to the front waist member's inner and outer sheets 24, 25 and the rear waist member's inner and outer sheets 34, 35, respectively, in the same manner as in the case of the appendix section elastic 51 or by adhesive applied to the respective sheets.

The crotch member 40 includes a liquid-absorbent structure 41, the gasket cuffs 70 and the leak-barrier cuffs 80. The liquid-absorbent structure 41 comprises a liquid-absorbent core 41a, an inner sheet 42 lying on the skin-facing side to cover the inner surface of the core 41a, a leak-barrier sheet 43 covering the outer surface of the core 41a and an outer sheet 44 lying on the garment-facing side (non-skin-facing side) of the leak-barrier sheet 43. As material for the core 41a, for example, fluff pulp fibers and/or super-absorbent polymer particles may be used. The core 41a has a length dimension in the transverse direction X gradually reduced toward the imaginary transverse center line Q-Q to be concave in the vicinity of the imaginary transverse center line Q-Q.

Both the inner sheet 42 and the leak-barrier sheet 43 are dimensioned to be larger than the core 41a in the longitudinal direction Y. Consequently, the core 41a is not present in the vicinity of the front and rear ends of the crotch member 40 in the longitudinal direction Y and the inner sheet 42 cooperates with the leak-barrier sheet 43 to form front and rear end flaps 45, 46. In these front and rear end flaps 45, 46, the inner sheet 42 and the leak-barrier sheet 43 are directly bonded to each other by bonding means such as hot melt adhesive.

In the transverse direction X also, the inner sheet 42 and the leak-barrier sheet 43 extending outward beyond the core 41a to form opposite side flaps 49 extending in the longitudinal direction Y of the crotch member 40. In the side flaps 49, the inner sheet 42 and the leak-barrier sheet 43 are directly bonded to each other by bonding means such as hot melt adhesive.

As stock material for the inner sheet 42, a liquid-pervious fibrous non-woven fabric such as an air-through fibrous non-woven fabric, a point bonded fibrous non-woven fabric or a spun bonded fibrous non-woven fabric having a basis mass in a range of about 10 to about 30 g/m$^2$ may be used.

As stock material for the leak-barrier sheet 43, a moisture-pervious but liquid-impervious plastic film may be used and the liquid-absorbent structure 41 may be entirely covered with the leak-barrier sheet 43 to prevent bodily fluids such as urine from leaking out from the diaper 10.

As stock material for the outer sheet 44, a moisture-pervious but liquid-impervious fibrous non-woven fabric such as a spun bonded/melt blown/spun bonded (SMS) fibrous non-woven fabric, a point bonded fibrous non-woven fabric or a spun bonded fibrous non-woven fabric having a basis mass in a range of 10 to 25 g/m² may be used.

Referring to FIG. 3, the crotch member 40 is bonded at its front and rear sections inclusive of the front and rear flaps 45, 46 to the front and rear waist members 20, 30, respectively, to form front and rear bonded regions 61, 62. These front and rear bonded regions 61, 62 are formed between the outer sheet 44 of the crotch member 40 and the inner sheets 24, 34 of the front and rear waist members 20, 30. While these front and rear bonded regions 61, 62 are formed over almost the entire areas in which the crotch member 40 overlaps with the front and rear waist members 20, 30, front and rear non-bonded regions 23, 33 are left free from bonding in the vicinity of the inner ends 23, 33 of the front and rear waist members 20, 30, respectively. It may be optionally designed whether the front waist elastic 26 and/or the appendix section elastic 51 are arranged in these front and rear non-bonded regions 63, 64.

The crotch member 40 joined to the front and rear waist members 20, 30 in this manner is provided on its skin-facing side with front and rear cover sheets 27, 37 serving to cover the front and rear ends 47, 48, respectively, of the crotch member 40. These front and rear cover sheets 27, 37 extend between respective pairs of opposite side edges 21, 31 of the front and rear waist members 20, 30 in the transverse direction X to cover the whole areas of the front and rear ends 47, 48 of the crotch member 40. These front and rear cover sheets 27, 37 cover the front and rear ends 47, 48 in this manner and thereby prevent so-called skin trouble due to contact of the front and rear ends 47, 48 with the wearer's skin.

In the crotch member 40 includes the gasket cuffs 70 and the leak-barrier cuffs 80 both formed of the outer sheet 44. The gasket cuffs 70 are formed of the outer sheet 44 extending on the outer surface of the core 41a and further outward beyond the side edges of the core 41a and then folded back in the transverse direction X. The leak-barrier cuffs 80 are contiguous to the respective gasket cuffs 70 and folded in Z-like-shape to be formed above the liquid-absorbent structure 41 (See FIGS. 4 through 8).

The side flaps 49 respectively have gasket elastics 71 including a plurality of elastic strings, extending in the longitudinal direction Y and attached under tension in a contractible manner thereto to elasticize the gasket cuffs 70 in the longitudinal direction Y. As the gasket elastics 71, elastic strings each having fineness in a range of about 470 to 1240dtex may be attached at a stretch ratio in a range of about 2.3 to about 3.0. In the present embodiment, the elastic strings each having fineness of about 470dtex are used as the gasket elastics 71 and attached at a stretch ratio of 2.7. The side edges of the leak-barrier sheet 43 underlying the liquid-absorbent structure 41 and extending outward beyond the side edges of the liquid-absorbent structure 41 extend into the associated side flaps 49, more specifically, between respective two layers of the side flaps 49 formed by folding back the side edges of the outer sheet 44. On the inner surface of the side flap 49 folded back in two layers, the outer sheet 44, the leak-barrier sheet 43 and the gasket elastics 71 are bonded together by bonding means such as adhesive to form gaskets' bonded regions 72. The gaskets' bonded regions 72 continuously extend in the longitudinal direction Y of the crotch member 40, respectively.

One end 71a of the gasket elastic 71 overlaps with the front waist elastic 26 and the other end 71b overlaps with the appendix section elastic 51 (See FIG. 2). The end 71a overlaps with the front bonded region 61 also and the other end 71b overlaps with the rear bonded region 62 also. In other words, the gasket elastic 71 is indirectly bonded to the front bonded region 61 by the one end 71a overlapping with the front waist elastic 26 and indirectly bonded to the rear bonded region 62 by the other end 71b overlapping with the appendix section elastic 51. Consequentially, the gasket elastics 71 attached to the inner surface of the outer sheet 44 outside the side edges of the core 41a are pulled outward in the transverse direction X as the front waist elastic 26 and the appendix section elastic 51 are stretched in the transverse direction X whereby the crotch member 40 is in contact with the wearer's body over the wide range. Such arrangement is effective also to prevent the front and rear ends of the core 41a from getting wrinkled to cause leakage of bodily fluids such as urine. Furthermore, such unique arrangement that the gasket elastics 71 overlap with the front waist elastic 26 and the appendix section elastic 51 allows the crotch member 40 to move integrally with the front and rear waist members 20, 30. As an advantageous consequence, it is possible to prevent the crotch member 40 from being left slipped down and to prevent the crotch member 40 from being unintentionally displaced relatively to the wearer's body. To keep stable of the crotch member 40 with the front and rear waist members 20, 30, the gasket elastics 71 preferably overlap with and are bonded together with at least one of the elastic string of the appendix section elastic 51 being nearest to the waist fit region 30a, more preferably with two or more of the elastic strings of the appendix section elastic 51 and most preferably with all of them. From the viewpoint of stability of the front and rear waist members 20, 30 relative to the crotch member 40, the appendix section elastic 51 and the gasket elastics 71 preferably overlap one with another and are bonded together in a region on the side of the waist fit region 30a provided that the appendix section 30b is bisected in the longitudinal direction Y to define the region near to the waist fit region 30a and the region remote from the waist fit region 30a.

The gasket elastics 71 preferably overlap one with another and are bonded to the one of the elastic strings of the appendix section elastic 51 lying adjacent to the imaginary line 38 in order that unintentional movement of the crotch member 40 relative to the rear waist member 30 can be avoided. Particularly when the front and rear waist members 20, 30 as well as the crotch member 40 are separately prepared and are assembled together to form the diaper 10 as in the present embodiment, the crotch member 40 would otherwise be apt to move relatively to the front and rear waist members 20, 30. However, this can be effectively prevented by the unique arrangement as has been described above.

The gasket elastics 71 are not arranged to extend to the front and rear ends 47, 48 of the crotch member 40 but the non-contractible regions 73a, 73b are formed between the one end 71a and the front end 47 and between the other end 72b and the rear end 48, respectively, so that these non-bonded regions 73a, 73b may be free from the contractile force of the gasket elastics 71. Such non-contractible regions 73a, 73b may be formed by attaching none of elastic strings to these regions as in the case of the present embodiment or by cutting or heat-treating elastic strings once attached to these regions.

The leak-barrier cuffs 80 are formed of sleeves which are formed, in turn, of the outer sheet extending further inward from the gasket cuffs 70 and folded back. Within the leak-barrier cuffs 80, two or more elastic strings as barrier elastic 81 extending in the longitudinal direction Y are attached under tension but in contractible manner to elasticize the leak-barrier cuffs 80 in the longitudinal direction Y. In a consequence, as will be apparent from FIG. 8, the leak-barrier cuffs 80 are spaced upward from the inner sheet 42 to come in close contact with the wearer's inguinal regions and, at the same time, the gasket cuffs 70 elasticized by the gasket elastics also raise themselves to come in close contact around the wearer's thighs. In this way, the leak-barrier cuffs 80 cooperate with the gasket cuffs 70 to form the double cuffs serving to prevent leakage of bodily fluids such as urine which would otherwise occur around the thighs.

Each of the barrier elastics 81 has one end 81a and the other end 81b spaced from the front and rear ends 47, 48, respectively, more specifically, these ends 81a, 81b are positioned inboard of the front and rear end flaps 45, 46 as viewed in the longitudinal direction Y. The leak-barrier cuffs 80 are bonded to the inner sheet 42 in barrier bonded regions 82 defined outside the one end 81a and the other end 81b of the barrier elastics 81 as viewed in the longitudinal direction Y. This means that the leak-barrier cuffs 80 do not raise themselves at least in the barrier bonded regions 82. While the barrier bonded regions 82 extend from the front and rear flaps 45, 46 inward in the longitudinal direction Y, these flaps 45, 46 preferably at least do not extend to the appendix section 30b and do not overlap with the appendix section 30b. With such arrangement, the leak-barrier cuffs 80 can raise themselves in the appendix section 30b to come in close contact with the wearer's body. While the appendix section 30b is apt to be spaced from the wearer's body, the leak-barrier cuffs 80 are able to prevent leakage of bodily fluids such as urine which might otherwise occur.

In the diaper 10 as has been described above, the appendix section 30b formed in the rear waist region 12 is able to cover the wearer's buttock and thighs. Even if leakage of bodily fluids occurs in such region, the appendix section 30b will receive this and protect the wearer's garment from being soiled with bodily fluids. The appendix section 30b is provided with the appendix section elastic 51 to elasticize this section 30b in the transverse direction X so that the appendix section 30b can come in close contact with the wearer's buttock along its cup-like shape. Therefore, should bodily fluid leakage occur, such cup-like shape will make it possible to receive such leakage of bodily fluid. Particularly, the appendix section elastic 51 arranged to have the highest stretch ratio in the vicinity of the crotch region 13 facilitate the appendix section 30b having a rectangular initial shape as a whole to be deformed to the cup-like shape adapted to be put in close contact with the wearer's body. With such arrangement, the appendix section 30b would not be unintentionally bent or curled up.

Since the appendix section 30b is formed with none of seams 14, the inner and outer sheets 34, 35 in the appendix section 30b would not have stiffness due to the seams 14. In a consequence, flexible texture of these inner and outer sheets 34, 35 can be maintained and any irritation experienced by the wearer can be alleviated. As has previously been described, the rear non-bonded region 64 formed adjacent to the inner end 33 of the rear waist member 30 in the appendix section 30b allows the inner end 33 also to maintain flexible texture. If the rear non-bonded region 64 is not formed, adhesive might run off along the inner end 33 of the rear waist member 30, stick to the wearer's skin and irritate the wearer's skin. The rear non-bonded region 64 according to the present invention can reliably eliminate such possibility. The one of the elastic strings of the front waist elastic 26 and the one of the elastic strings of the appendix section elastic 51 both arranged in the front and rear bonded regions 61, 62, respectively to be adjacent to the imaginary transverse center line Q-Q are located in the vicinity of the boundary between these bonded regions 61, 62 and the front and rear non-bonded regions 63, 64, respectively. Such unique arrangement is effective to maintain flexibility of the front and rear non-bonded regions 63, 64 and to put the front waist region 11 and the appendix section 30b in close contact with the wearer's body. Provision of the appendix section 30b allows the area over which the crotch member 40 is put flat together with the rear waist member 30 to be sufficiently enlarged to prevent unintentional movement of the crotch member 40 relative to the rear waist member 30.

While the front and rear bonded regions 61, 62 are formed over almost the entire area in which the crotch member 40 overlaps with the front and rear waist members 20, 30 according to the present embodiment, it is also possible without departing from the scope of the invention to arrange so that the front and rear bonded regions are not formed in the both lateral zones of this overlapping area opposed to each other in the transverse direction X. Particularly the area in which the front and rear waist members 20, 30 overlap with the gasket elastic 71 may be partially left formed with neither the front nor the rear bonded regions to assure that the gasket cuffs 70 can be separated from the front and rear waist members 20, 30 and come in close contact with the wearer's body.

<Second Embodiment>

Figure 9:
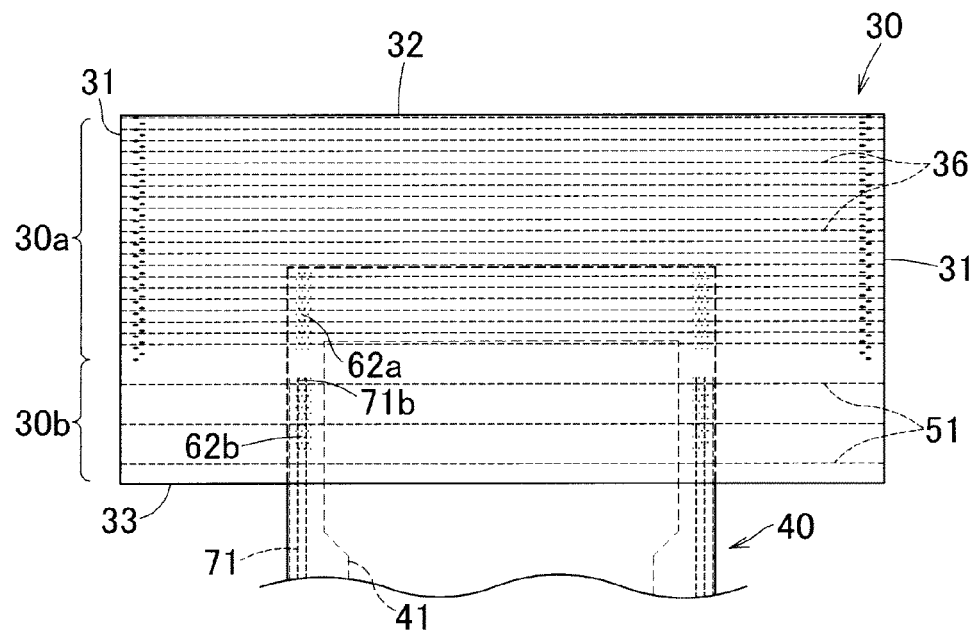
FIG. 9 is a partial diagram illustrating a diaper according to a second embodiment of the present invention.

FIG. 9 is a view substantially similar to FIG. 3, showing a second embodiment of the present invention. The second embodiment is characterized in that the rear bonded region 62 comprises first and second bonded regions 62a, 62b spaced from each other in the longitudinal direction Y. The basic aspect other than the characteristics described above is similar to the first embodiment and the following description will be limited to the aspect differing from the first embodiment and, in FIG. 9, the components which are the same as those in the first embodiment are designated with same reference numerals.

The first bonded region 62a is located in the waist fit region 30a of the rear waist member 30 and the second bonded region 62b is located in the appendix section 30b. These first and second bonded regions 62a, 62b are formed to be spaced from each other in the longitudinal direction Y and the second bonded region 62b is located outboard of the one of the appendix section elastic 51 as viewed in the longitudinal direction Y, in other words, located rather in the vicinity of the outer end of the rear waist member 30.

By spacing the first and second bonded regions 62a, 62b from each other, a quantity of adhesive to be used can be reduced and thereby stiffness of the rear waist member 30 and the crotch member 40 may be prevented from increasing due to the presence of adhesive.

While both the first embodiment and the second embodiment of the present invention has been exemplarily described hereinabove as so-called three-piece diaper comprising the front and rear waist members 20, 30 and the crotch member 40 prepared as the separate members wherein the front and rear members 20, 30 are connected to each other by the crotch member 40, the present invention is not limited to such three-piece diaper. The present invention is applicable to the diaper comprising these three members continuously formed. However, it should be appreciated that the effect of the present invention can be most prominently expressed in such three-piece diaper. In the conventional diaper comprising the front waist member, the rear waist member and the crotch member separately prepared and then assembled together, the crotch member is apt to move particularly in the transverse direction X relatively to the front and rear waist members. To overcome this problem, according to the present invention, the rear waist member 30 is provided with the appendix section 30b to enlarge the area in which the rear waist member 30 overlaps with the crotch region 40, on one hand, and to assure that the gasket elastic 71 attached to the crotch member 40 overlaps with and is bonded to the appendix section elastic 51. With such arrangement, unintentional movement of the crotch member 40 relative to the rear waist member 30 is restricted. Particularly the gasket elastic 71 and the appendix section elastic 51 are fixed to each other at two locations in the transverse direction X and the unintentional displacement is reliably restricted. Assumed that a mother holds her baby on baby's buttocks, even if the mother's arm moves along the baby's buttocks, the diaper 10 would not be displaced relatively to the baby's body.

While the front and rear waist elastics 26, 36 have been described above to extend continuously from the one side edge 21, 31 to the other side edge 21, 31, it is possible, for example to cut these elastics 26, 36 in the region overlapping with the core 41a so that the core 41a is not affected by contractile force of these elastics 26, 36. The same effect may be achieved also by the other means such as adhesive fixation.

While a plurality of elastic strings are used to elasticize the front and rear waist members 20, 30 in the transverse direction X according to the illustrated embodiments, the elasticizing means is not limited to such strings and the other various elastic materials such as the elastic sheet or elastic belt may be also used. This is true for the gasket elastic 71 and the barrier elastic 81. While the liquid-absorbent structure 41 having the length dimension in the transverse direction X gradually reduced from the front and rear end portions toward the middle portion is used in the illustrated embodiments, it is also possible to use the square-shaped liquid-absorbent structure.

While the appendix section 30b is rectangular in the illustrated embodiments, it is also possible to the appendix section 30b having corners defined by the side edges 31 and the inner end 33 of the rear waist member 30 are rounded. Such appendix section 30b more easily comes in close contact with the wearer's body.

The aspects of the present invention described above may be arranged in at least the following item(s):

(i) A wearing article (10) comprising a chassis, a liquid-absorbent structure (41) and a pair of gasket cuffs (70), the chassis having a longitudinal direction (Y), a transverse direction (X), a skin-facing side, a non-skin-facing side, a front waist region (11), a rear waist region (12) and a crotch region (13) extending between the front and rear waist regions, the liquid-absorbent structure extending across the crotch region into the front and rear waist regions, and the gasket cuffs being outboard of the liquid-absorbent structure in the transverse direction, wherein the front and rear waist regions include front and rear waist elastics (26, 36) attached thereto in a contractible manner in the transverse direction and the gasket cuffs include gasket elastics (71) attached thereto in a contractible manner in the longitudinal direction wherein: the rear waist region comprises a waist fit section (30a) extending in a vicinity of a waist opening and an appendix section (30b) arranged to be contiguous to the waist fit section and lying in the crotch region, wherein the rear waist elastic (36) is attached to the waist fit section and the appendix section is provided with an appendix section elastic (51) attached thereto in contractible manner in the transverse direction; and the gasket elastic has one end overlapping with and bonded to the front waist elastic and other end overlapping with and bonded to the appendix section elastic.

The aspect of the present invention described in the above item (i) may provide one or more of the following advantageous effects:

(a) With unique arrangement as described above, the front and rear waist regions are cooperatively movable by the intermediary of the gasket elastic and thereby any unintentional displacement of the crotch region can be prevented.

Additionally, one or more of the following embodiments are provided in accordance with further aspects:

(ii) Both the appendix section elastic and the rear waist elastic comprise a plurality of elastic strings spaced one from another in the longitudinal direction and a distance between a pair of the adjacent elastic strings of the appendix section elastic is set to be larger than that of the rear waist elastic.

(iii) The chassis includes a front waist member (20) defining the front waist region, a rear waist member (30) spaced from the front waist member in the longitudinal direction and defining the rear waist region and a crotch member (40) defining the crotch region; and a front end of the crotch member include a front bonded region (61) bonded to the front waist member and a rear end of the crotch member includes a rear bonded region (62) bonded to the rear waist member and a rear non-bonded region inboard of the crotch member in the longitudinal direction and separated from the front waist member and the rear waist member.

(iv) The rear bonded region comprises a first bonded region (62a) and a second bonded region (62b) spaced from each other in the longitudinal direction.

(v) The first bonded region and the second bonded region are formed to overlap with the gasket elastic.

(vi) The front waist region and rear waist region are bonded together along respective both side edges (21, 31) by seams (14) and the appendix section is formed with none of the seams.

According to the embodiments in the above (ii) to (vi), the advantageous effect(s) set forth at (a) is/are better ensured. Further advantageous effects of the respective embodiments may be obtained as discussed in the respective related descriptions.

The terms "first" and "second" herein are used merely for distinguishing between similar elements.

The invention claimed is:
1. A wearing article comprising:
a chassis;
a liquid-absorbent structure; and
a pair of gasket cuffs,
said chassis having:
   a longitudinal direction;
   a transverse direction;
   a skin-facing side;
   a non-skin-facing side;
   a front waist region, a rear waist region; and
   a crotch region extending between said front and rear waist regions,
said liquid-absorbent structure extending across said crotch region into said front and rear waist regions, and
said gasket cuffs being outboard of said liquid-absorbent structure in said transverse direction,
wherein said front and rear waist regions include a front waist elastic and a rear waist elastic, respectively, attached thereto in a contractible manner in said transverse direction and said gasket cuffs include gasket elastics attached thereto in a contractible manner to exert a contractile force in said longitudinal direction wherein:
said chassis includes a front waist member defining said front waist region, a rear waist member spaced from said front waist member in said longitudinal direction and a crotch member defining said crotch region, and
said rear waist member comprises:

a waist fit section extending adjacent to a waist opening and defining said rear waist region; and an appendix section arranged to be contiguous to said waist fit section and lying in said crotch region, wherein said rear waist elastic is attached to said waist fit section and said appendix section is provided with an appendix section elastic attached thereto in contractible manner in said transverse direction;

said gasket elastics have one end overlapping with and bonded to said front waist elastic and another end overlapping with and bonded to said appendix section elastic and spaced from a rear end of said crotch member; and such that a region free from the contractile force of the gasket elastics is formed between said another end of said gasket elastics and said rear end of said crotch member, and wherein both said appendix section elastic and said rear waist elastic comprise a plurality of elastic strings spaced one from another in said longitudinal direction and a distance between any two adjacent elastic strings of said appendix section elastic is set to be larger than that of said rear waist elastic.

2. The wearing article defined by claim 1, wherein:

a front end of said crotch member includes a front bonded region bonded to said front waist member and a rear end of said crotch member includes a rear bonded region bonded to said rear waist member and a rear non-bonded region inboard of said crotch member in said longitudinal direction and separated from said front waist member and said rear waist member.

3. The wearing article defined by claim 2, wherein said rear bonded region comprises a first bonded region and a second bonded region spaced from each other in said longitudinal direction.

4. The wearing article defined by claim 3, wherein one of said first bonded region and said second bonded region is formed to overlap with said gasket elastics.

5. The wearing article defined by claim 1, wherein transverse sides of the appendix section are parallel.

6. The wearing article defined by claim 2, wherein said front waist region and rear waist region are bonded together along respective side edges by seams and said appendix section is formed with none of said seams.

7. The wearing article defined by claim 3, wherein said front waist region and rear waist region are bonded together along respective side edges by seams and said appendix section is formed with none of said seams.

8. The wearing article defined by claim 4, wherein said front waist region and rear waist region are bonded together along respective side edges by seams and said appendix section is formed with none of said seams.

* * * * *